US008082108B2

(12) United States Patent
Fitch et al.

(10) Patent No.: US 8,082,108 B2
(45) Date of Patent: *Dec. 20, 2011

(54) PAIRWISE FRAGMENT INTERACTION COMPUTATION

(75) Inventors: Blake G. Fitch, White Plains, NY (US); Robert S. Germain, Larchmont, NY (US); Michael G. Pitman, Wappingers Falls, NY (US); Aleksandr Rayshubskiy, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 521 days.

This patent is subject to a terminal disclaimer.

(21) Appl. No.: 11/926,492

(22) Filed: Oct. 29, 2007

(65) Prior Publication Data

US 2008/0183435 A1     Jul. 31, 2008

Related U.S. Application Data

(62) Division of application No. 11/113,939, filed on Apr. 25, 2005, now abandoned.

(51) Int. Cl.
*G06F 19/00* (2011.01)
*G06F 17/00* (2006.01)
*G01N 33/48* (2006.01)

(52) U.S. Cl. .................................. 702/19; 702/20; 703/2

(58) Field of Classification Search ................ None
See application file for complete search history.

(56) References Cited

OTHER PUBLICATIONS

Nyland et al., Achieving Scalable parallel Molecular Dynamics Using Dynamic Spatial Domain Decomposition Techniques, 1997, Journal of Parallel and Distributed Computing, vol. 47, pp. 125-138.*
Nakano, Aiichiro, Multiresolution Load Balancing in Curved Space: the wavelet representation, 1999, Concurrency: Practice and Experience, vol. 11, pp. 343-353.*
IBM Blue Gene team, "Blue Gene: A vision for protein science using a petaflop supercomputer." 2001.
T. P. Straatsma, J. A. McCammon, "Load balancing of molecular dynamics simulation with NWChem." 2201.
The BlueGene/L Team, "An overview of the BlueGene/L supercomputer." 2002.

* cited by examiner

*Primary Examiner* — Jason Sims
(74) *Attorney, Agent, or Firm* — Michael J. Buchenhomer; Vaken Alexanian

(57) ABSTRACT

An information processing system includes a processor configured for: defining a simulation space comprising a plurality of fragments and a plurality of processing nodes; determining a weight corresponding to the computational cost for a given pairwise fragment interaction; assigning the weight to the simulation space at a point between the two interacting fragments; performing a spatial partitioning of a volume of the simulation space such that all partitions have substantially the same weight; and assigning a computation of the pairwise fragment interaction to any node that has the positions of both groups of fragments.

14 Claims, 4 Drawing Sheets

PAIRWISE FRAGMENT INTERACTION COMPUTATION

CROSS-REFERENCE TO RELATED APPLICATIONS

This application is a division of commonly-owned, U.S. application Ser. No. 11/113,939, filed on Apr. 25, 2005, now abandoned which is incorporated by reference as if fully set forth herein.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of information processing systems and methods and more particularly relates to supercomputer systems and methods used for n-body simulations including bio-molecular simulations and processing such as protein and deoxyribonucleic acid (DNA) folding.

BACKGROUND OF THE INVENTION

Bio-technology has substantially advanced in parallel with the use of powerful information processing systems. One such system is the BLUE GENE® Project announced in 1999. BLUE GENE is a registered trademark of International Business Machines Corporation. At that time, the BLUE GENE® Project had two high level goals: to build the world's fastest super computer and to use this unprecedented computational resource to solve the grand challenge life sciences problems such as advancing our understanding of biologically important processes, in particular, the mechanisms behind protein folding.

As a step on the way to achieving the first of these goals, the first member of the BLUE GENE® parallel computation platform (BLUE GENE) family, BLUE GENE/L®, was designed and built. In order to address the second of these goals, a research project was begun to create a classical molecular dynamics software package targeted at the Blue Gene/L architecture and to use that package for long-time and large-scale bio-molecular simulations.

Classical molecular dynamics is predominantly an n-body problem. A standard definition of an n-body problem is as follows: The n-body problem is the problem of finding, given the initial positions, masses, and velocities of n bodies, their subsequent motions as determined by classical mechanics.

An n-body problem, for example molecular dynamics (MD), proceeds as a sequence of simulation time steps. At each time step, forces on particles, in MD atoms, are computed; and then the equations of motion are integrated to update the velocities and positions of the particles. In order to compute the forces on the particles, nominally the force between each particle and every other particle is computed, a computational burden of $0(n^2)$.

Practically speaking, molecular dynamics programs reduce the $0$ $(n^2)$ by cutting off pair interactions at some distance. However for many scientifically relevant molecular systems, the computational burden due to the particle pair interactions remains large. In order to reach scientifically relevant simulation times, parallel computers are required to compute particle pair interactions rapidly. Note that the BLUE GENE/L® parallel computational platform does interprocessor communication primarily using a 3D torus network. Processor space is defined by the location of processors on the 3D torus network and communication costs between processors increase with distance.

There is a need for a system and method to enable the geometric n-body problem to be efficiently mapped (e.g., to a machine with a fundamentally geometric processor space such as BLUE GENE/L®).

SUMMARY OF THE INVENTION

Briefly, according to an embodiment of the invention, an information processing system includes a processor configured for: defining a simulation space comprising a plurality of fragments and a plurality of processing nodes; determining a weight corresponding to the computational cost for a given pairwise fragment interaction; assigning the weight to the simulation space at a point between the two interacting fragments; performing a spatial partitioning of a volume of the simulation space such that all partitions have substantially the same weight; and assigning a computation of the pairwise fragment interaction to any node that has the positions of both groups of fragments.

The method can also be implemented as machine executable instructions executed by a programmable information processing system or as hard coded logic in a specialized computing apparatus such as an application-specific integrated circuit (ASIC).

DETAILED DESCRIPTION

In the discussion that follows we will use the following definitions/conventions:

For some n-body simulations, it is convenient to define a partitioning of the particles into groups of one or more particles that are treated as a unit for certain purposes. When this intended, the term "fragment" will be used to indicate such an entity that consists of one or more particles.

The term "node" refers to the computational elements that form nodes in the graph defined by the interconnection network. Any "node" may include one or more processors. The internal operations of a node are known to those with knowledge in the art and will not be addressed in this discussion.

The term "simulation space" refers to the domain of the n-body simulation.

The term "node space" refers to the geometry of the interconnections between nodes of the machine. Typically we will be discussing a machine with a three-dimensional torus/mesh interconnect geometry in which each node is connected to its six nearest neighbors and is addressed by a triple of integers that represent its coordinates within the network. In a torus, periodic boundary conditions are implemented physically by connecting the nodes on opposite "faces" of the machine.

Figure 1:
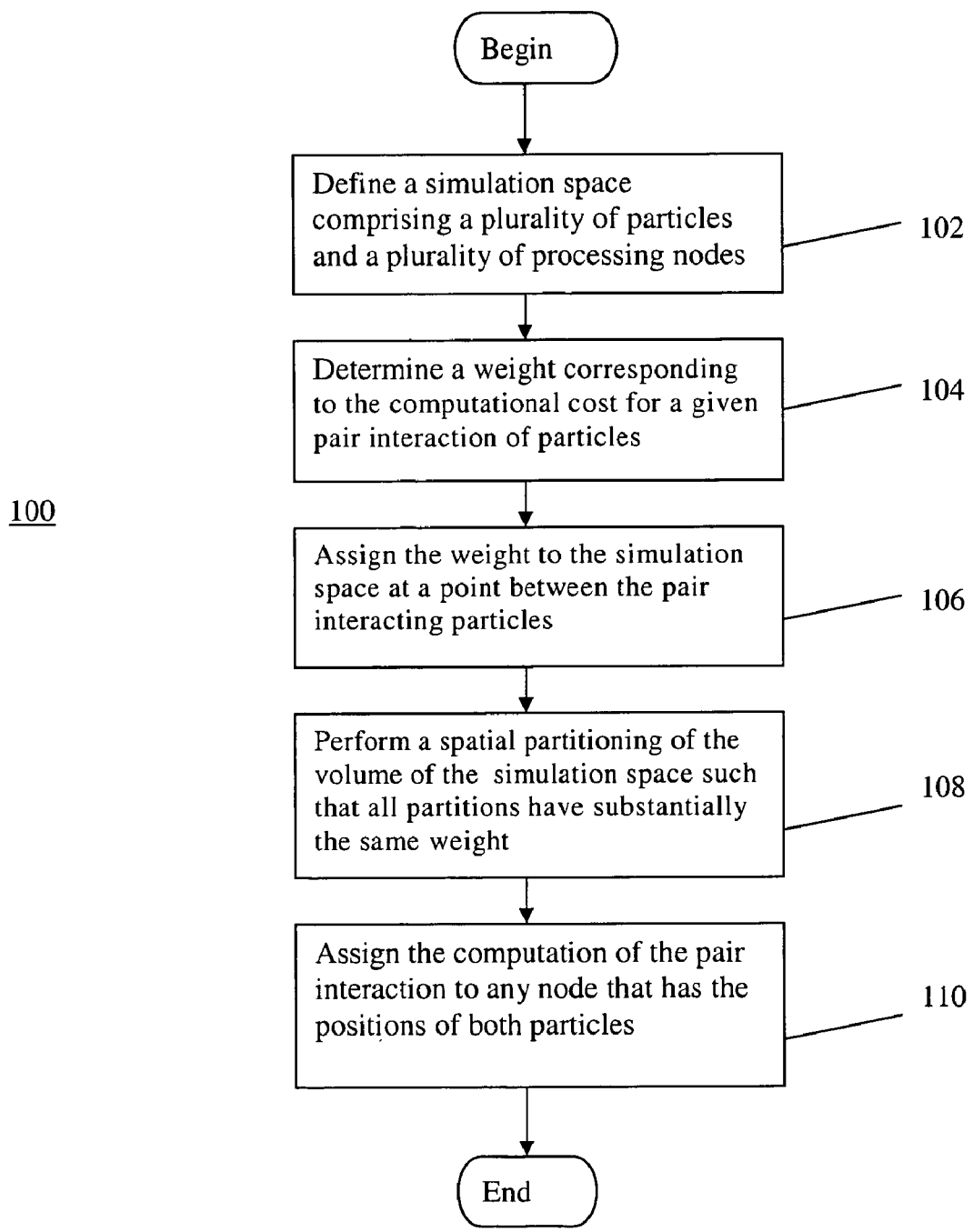
FIG. 1 is a flowchart of a method according to an embodiment of the invention.

Referring to FIG. 1, there is shown a flow chart illustrating a method 100, according to an embodiment of the invention, for creating a load balanced spatial partitioning of a structured, diffusing system of particles with pairwise interactions that is scalable to a very large number of nodes and has favorable communications characteristics.

Step 102 defines a simulation space comprising a plurality of particles and a plurality of processor nodes. This step 102 can be performed using a k-d tree on the simulation space. To deal with structural imbalance in the node space, step 104 determines a weight corresponding to the computational cost for a particular pair interaction of particles, or locally clustered groups of particles, to simulation space at a point between these fragments, such as the midpoint of the distance between the fragments. Each of the fragments can comprise a single particle.

Step 106 assigns the determined weight to a point in simulation space between the locations of the two interacting particles. The point is preferably the midpoint between the interacting fragments. The position of each particle is broadcast to points in simulation space within a distance of on-half of the cut-off radius.

Step 108 performs a spatial partitioning of the volume of the simulation space such that all partitions have substantially the same weight. Step 110 assigns a computation of the fragment pair interaction to any node that has the positions of both fragments.

To simplify the processing, pair interactions can be cut off beyond a defined radius $R_c$, therefore one can broadcast the position of a particle to the group of nodes containing a portion of the sphere of radius $R_b > R_c/2$ in simulation space, ensuring the existence of at least one node containing the positions of both particles required to compute any interaction. When more than one node contains the positions required to compute an interaction, the computation can be assigned to any of those nodes, providing an opportunity for eliminating imbalances caused by short term local fluctuations in interaction workload. Because we are carrying out the load-balancing using interaction centers, there are many more geometrically distinct work objects that can be partitioned using an ORB strategy and this decomposition allows productive use of more nodes than there are particles in the system.

Although in the embodiments discussed herein the method is performed with a processor node network comprising a toroidal shape, the method may be applied to other network topologies with good results.

Figure 2:
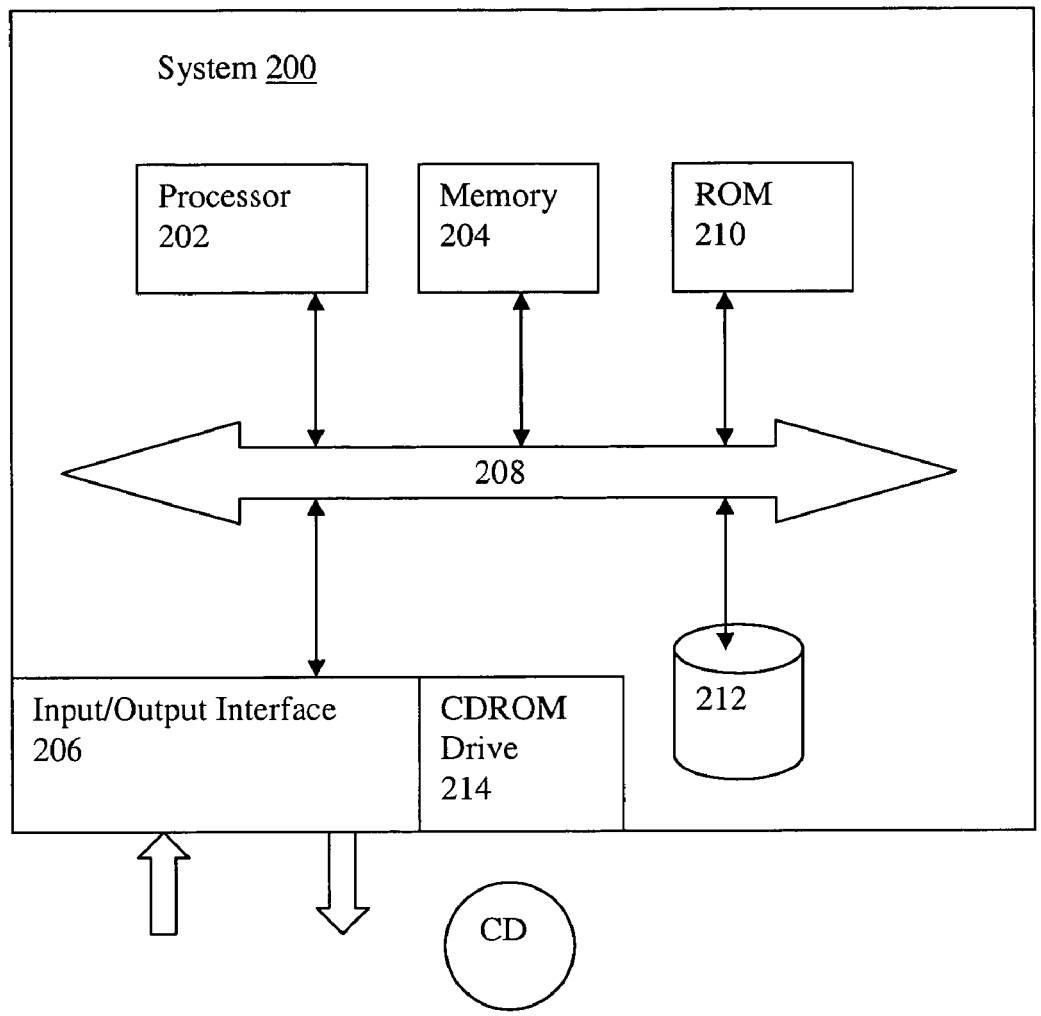
FIG. 2 is a high level block diagram showing an information processing system according to another embodiment of the invention.

Referring to FIG. 2, there is shown a block diagram of an information handling system 200 configured to operate according to an embodiment of the invention. The system 200 represents a processing node in a multi-processor node network. The system 200 comprises a processor 202, a memory 204, and an input/output (I/O) subsystem 206.

The memory 204 can be a volatile or non-volatile random-access memory (RAM). The system 200 can also comprise read-only memory (ROM) 210 and a magnetic media mass storage device such as a hard disk drive 212. These are linked by a CPU bus 208.

The I/O subsystem 206 may further comprise various end user interfaces such as a display, a keyboard, and a mouse. The I/O subsystem 206 may further comprise a connection to a network such as a local-area network (LAN) or side-area network (WAN) such as the Internet. According to another embodiment of the invention, a computer readable medium, such as a CDROM 214 can include program instructions for operating the programmable computer 200 according to the invention. What has been shown and discussed is a highly-simplified depiction of a programmable computer apparatus. Those skilled in the art will appreciate that other low-level components and connections are required in any practical application of a computer apparatus.

An embodiment of the invention efficiently solves the N-body problem by geometrically mapping simulation space to a torus/mesh parallel computer's node space, a spatial decomposition. The essential mechanism for distributing the work is an ellipsoidal broadcast of particle positions followed possibly by an ellipsoidal reduction of forces on fragment home nodes.

Ellipsoidal Communication Primitives

Ellipsoidal communication primitives are a basic requirement for this embodiment. These can be constructed using point-to-point communications; however, hardware may offer features to enhance the performance of these primitives such as multi-cast. For the purposes of this discussion, we will describe the functional requirements of ellipsoidal communication primitives but not the implementation.

In our mapping of simulation space to node space, we divide simulation space into the same number of sub-volumes as we have nodes and further, the simulation space will have the same extents (measured in voxels) in each dimension as node space (measured in nodes). The volume elements assigned to each processor (or voxels) may be of non-uniform size.

Ellipsoidal communications patterns in node space arise when spherically bounded communication patterns in simulation space are carried out and when the voxels in simulation space are non-uniform in size or non-cubical. The two operations of interest are: (1) Ellipsoidal broadcast: given a sphere in simulation space, broadcast data from the center to each node managing space in that sphere; and (2) Ellipsoidal reduce: given a sphere in simulation space, theta-reduce data from each node managing space in that sphere to the root at the center.

N-Body Spatial Decomposition for Load Balance

N-body problems in a periodic simulation space nominally have a computational burden defined by the order $O(N^2)$ pairwise particle interactions possible. In many applications, this computational burden is reduced to $O(N)$ by cutting off (i.e., not computing) interactions between particles separated by more than a specified distance in periodic simulation space.

A natural way to map a spatial problem on a spatial connected machine is with a direct mapping where the simulation space is uniformly assigned to the processors' space. For N-body systems (assuming that all pair interactions have the same computational cost) with a uniform density of particles or where no cut-offs are imposed, this simple mapping will result in a balanced load across the machine since each node or region of nodes will have roughly the same interaction computation workload.

Where particles are not evenly distributed in the simulation space and interaction cutoffs are in effect and/or interaction computation costs are not the same, a direct mapping results in load imbalance. There are techniques for locally averaging load imbalance between nodes. However, if the imbalance is severe enough, these regional averaging techniques can be ineffective.

For any fixed distribution of particles, techniques such as optimal recursive bisection (ORB) can be used to balance computational burden on each node by assigning partitioning simulation space into non-uniform sub-volumes that will be assigned to nodes. See L. Nyland, J. Prins, R. H. Yun, J. Hermans, H.-C. Kum, and L. Wang. Achieving scalable parallel molecular dynamics using dynamic spatial decomposition techniques. Journal of Parallel and Distributed Computing, 47(2):125-138, 1997.

An ORB can be constructed from a distribution of points representing particle or fragment centers, or as discussed below, midpoints of pair interactions. Prior to ORB construction, a function estimating the work associated with each point is evaluated and stored with the point. In the case of pair interaction midpoints, this corresponds to the work required to evaluate the forces between the pair of particles or fragments. ORB construction begins with the periodic boundaries of the simulation cell as the initial volume, and the distribution of points with their associated work values. Application of the ORB technique partitions a unit cell into 2N smaller cells. For cases where N is divisible by 3, the number of subvolumes will be equal in each dimension (number of subvolumes=8, 64, 512, 4096, . . . ).

The simulation cell volume is partitioned recursively in cycles. Each cycle bisects a volume along each dimension in succession giving eight subvolumes at the end of the cycle. Each bisection begins by sorting the distribution of points within the volume along one of its dimensions and locating the nearest point to the median of the distribution of work values associated with each point. The volume is then divided with a plane orthogonal to the sorted dimension passing through the selected point. The points in the subvolumes on either side of the plane are then each separately sorted along another dimension, and partitioned according to the points near the median of the work distribution for their respective work value distributions. Each of the four resulting subvolumes are then sorted in the final dimension and partitioned, giving eight partitions of the original volume. This cycle repeats recursively for each of the eight subvolumes until the desired number of subvolumes is reached, which is equal to the number of nodes to be used in the simulation. For cases where N is not divisible by three, the initial cycle partitions along either one or two dimensions, rather than three. The remaining cycles will then partition along each of the three dimensions.

The resulting ORB partitioning of simulation space greatly reduces the variance of work needed to compute the forces represented by the points in a given subvolume. The assignment of the work represented by the points in each subvolume to a node therefore provides an initial step in load balancing. A given N-body problem may require multiple load balancing techniques. An ORB may be required to balance the global imbalance caused by the structure of the system being simulated and a local work exchange scheme may be required for imbalances caused by diffusion. See T. P. Straatsma and J. A. McCammon. Load balancing of molecular dynamics simulation with NWChem. IBM Systems Journal, 40(2):328-341, 2001.

Molecular Dynamics Decompositions Based on Ellipsoidal Communications Primitives Optimal Interaction Assignment Using ORBs and Dynamic Interaction Balancing.

Molecular dynamics as applied to biomolecular simulation of fixed sized problems on very large, geometric node spaces requires a simulation space to node space mapping that maintains as much locality as possible while balancing workload. This is so that communication costs and computational costs are minimized in balance.

Since our n-body problem has structural imbalance caused by inhomogeneities in the system, we create a partition of simulation space based on ORB that divides the workload evenly assuming a nominal weight for each pair interaction and a specified cutoff. In the event that the ratio of the number of particles to node count is small, it may be desirable to start dividing simulation space using optimal recursive bisection and then switch to a strict volumetric bisection near the leaves to improve micro level balance of particle assignment.

Figure 3:
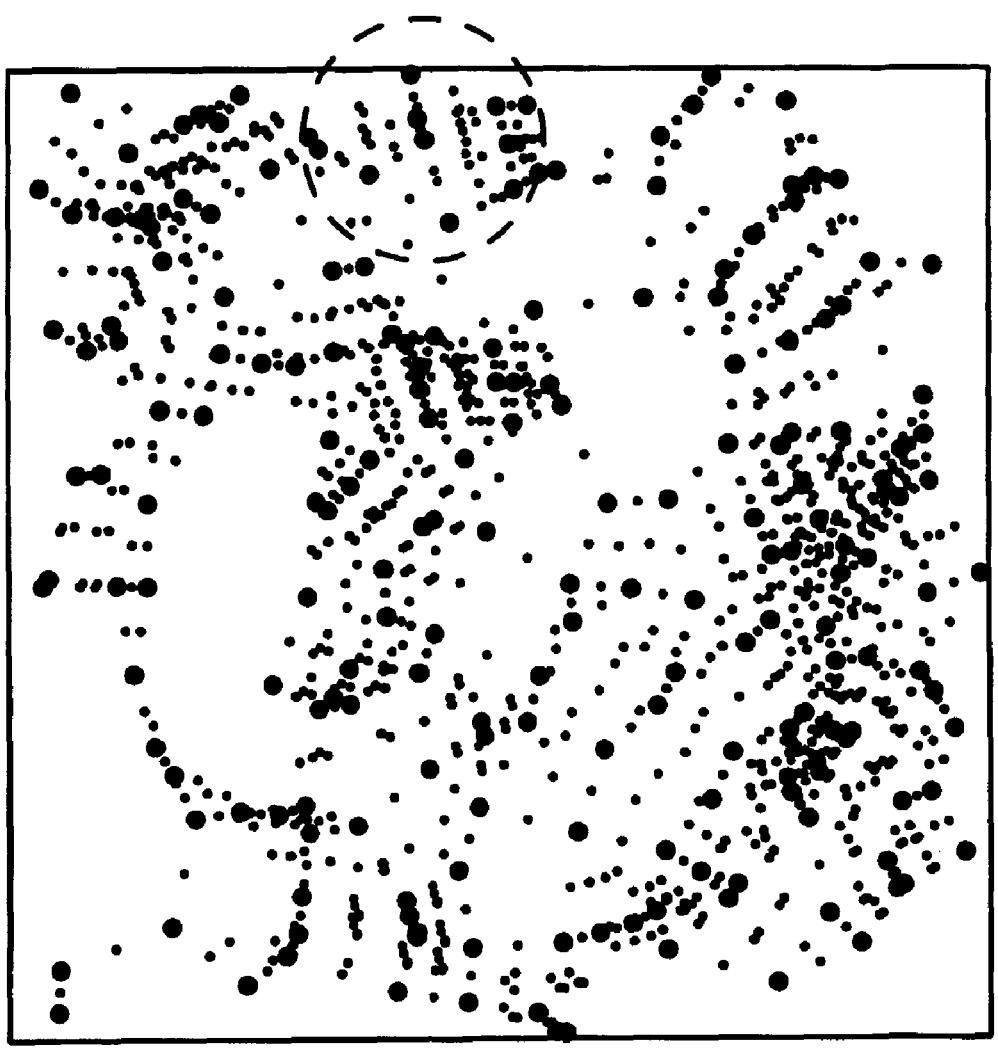
FIG. 3 is a view of a two-dimensional system with both particle positions and interaction centers shown.

FIG. 3 contains a view of a two-dimensional system with both particle positions and interaction centers shown. FIG. 3 illustrates the relationship of the particle positions (each shown as larger dots) and the interaction centers (each shown as a smaller dot) in simulation space. The interaction centers are placed at the mid-point between each pair of particles that fall within the cut-off radius. A dashed circle with radius equal to the cut-off radius ($r_c$) chosen is drawn around one of the particles. Static or "structural" load balancing is carried out by using optimal recursive bisection to partition the simulation volume into subvolumes that contain approximately equal computational burdens. The computational burden of a sub-volume is computed by summing the computational burden of each interaction center contained within that sub-volume.

Next, the minimal set of communicating nodes for a particular particle must be identified. The minimal set of communicating nodes is defined as all those nodes which contain any of the spherical volume of space (with radius greater than half the cutoff radius) centered about the particle. This defines a minimal volume in node space that ensures that there exists at least one node for every pair of particles within cutoff that can calculate the interaction between that pair.

During each simulation step, each node sends all its particle positions to each of its communication partners and receives from each a set of particle positions. A node may be assigned to evaluate the interaction between any pair of particles in the set of positions it has received.

Figure 4:
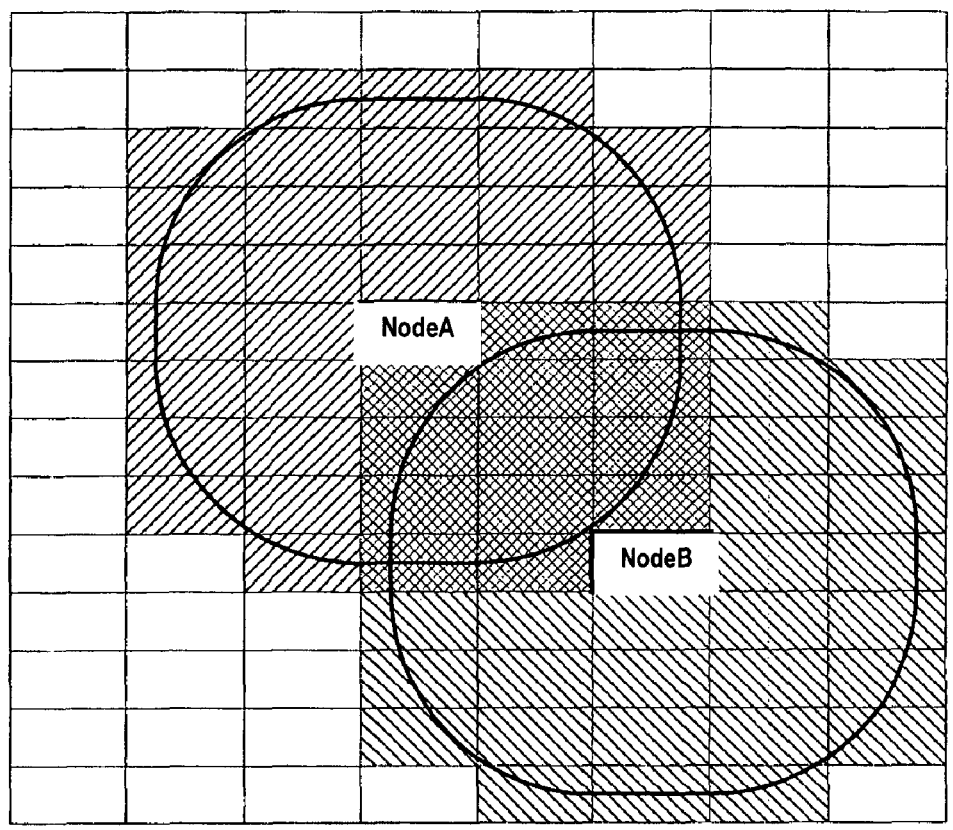
FIG. 4 shows a spatial decomposition showing the broadcast zones for two nodes superimposed on the spatial decomposition of the domain onto all nodes (two-dimensional view for simplicity).

Although pairs of particle positions in the simulation space separated by close to the cutoff distance might be received by only a single node creating a definitive assignment, generally the positions of any given pair of particles will be received by several nodes as shown in FIG. 4, any one of which may be assigned that pair's interaction.

Interaction assignment may be accomplished by any method which results in the interaction between a pair of particles being done once on one node. An example of a simple algorithm is to specify that the interaction will be done on the node that has received both particle positions and has the minimum node id number. Such algorithms however have load balancing characteristics which reflect the spatial mapping technique used.

In order to reduce micro load imbalance, dynamic deterministic interaction assignment can be employed. These techniques allow rapid overlapping regional averaging. To enable these techniques, each node must measure its current computational load and add this value to each message it sends to its communication partners. When a node receives its set of [load, position set] messages from its communicating partners, it now has enough information to deterministically assign itself a set of inter-actions. The set of interactions each node receives can contribute to load averaging among its communication partners.

For the purposes of increased scope for load balancing or in cases where communication costs are high relative to computation costs, it may be advantageous to increase the simulation space radius determining the communication partner set beyond Rd 2 to increase the number of nodes available for load balancing.

Referring to FIG. 4, there is illustrated a spatial decomposition showing the broadcast zones for two nodes (Node A and Node B) superimposed in the spatial decomposition of the domain onto all nodes (a two-dimensional view is shown for simplicity). The nodes that contain areas of simulation space within a distance $R_b$ of the voxel assigned to Node B are within an area shown with back hatching in the figure. The nodes that contain areas of simulation space within a distance $R_b$ of the voxel assigned to Node A are within an area with forward hatching. An overlap area 412 comprises nodes also contain areas of simulation space within $R_b$ of the voxels assigned to Nodes A and B. Radius $R_b$ is shown by ellipses surrounding Nodes A and B, respectively. Radius $R_b$ is greater than or equal to $R_c/2$, where $R_c$ is the cutoff radius. The interaction between a particle stored on Node A and a particle stored on Node B can be computed on any of the nodes within the cross hatched area.

Therefore, while there has been described what is presently considered to be the preferred embodiment, it will understood by those skilled in the art that other modifications can be made within the spirit of the invention.

The invention claimed is:

1. An information processing system comprising:
   a processor configured for:
   defining a three-dimensional simulation space comprising a plurality of fragments and a plurality of processor nodes by mapping said three-dimensional simulation space to node space, wherein said mapping comprises:
   identifying a cutoff area by cutting off pairwise interaction between particles beyond a defined radius;
   ensuring that there exists at least one processor node for every pair of particles within the cutoff area that can calculate the pairwise interaction by identifying a minimal set of communicating nodes for a particular particle as those nodes which contain any of the volume of space centered about the particle;
   dividing the three-dimensional simulation space into a same number of voxels as processor nodes;
   determining a weight corresponding to a computational cost for a given pairwise fragment interaction in the simulation space at a midpoint between the interacting particles within the defined radius;
   assigning the determined weight to the midpoint in the simulation space between the two interacting fragments;
   performing a spatial partitioning of a volume of the simulation space such that all partitions have substantially the same weight;
   assigning a computation of the pairwise interaction to the processing node owning the voxel that contains the midpoint of a line connecting the interacting pair of particles; and
   broadcasting the position of each particle to points in the simulation space within a distance of one-half of the cut-off radius.

2. The system of claim 1 wherein the processor is further configured for performing a spatial partitioning using a k-d tree on the simulation space.

3. The system of claim 1 wherein the processor is further configured for assigning a weight to centers of the groups of fragments.

4. The system of claim 1 wherein each of the fragments comprises a single particle.

5. The system of claim 1 wherein the processor is further configured for broadcasting the position of a particle to a group of nodes containing a portion of a sphere having a radius Rb that is greater than Rc/2, where Rc is the defined radius to ensure the existence of at least one node containing the positions of both particles in a fragment pair required to compute any interaction.

6. The system of claim 1 wherein the processor is further configured for when more than one node contains positions required to compute a particle interaction, the computation is assigned to any of those nodes, providing an opportunity for eliminating imbalances caused by short term local fluctuations in interaction workload.

7. The system of claim 1 wherein the plurality of processor nodes are used for n-body simulations.

8. The system of claim 7 wherein the n-body simulations comprise bio-molecular simulations.

9. A computer program product embodied on a non-transitory computer readable storage medium and comprising code that, when executed, causes a computer to perform the following:
   define a three-dimensional simulation space comprising a plurality of groups of particles and a plurality of processor nodes by mapping said three-dimensional simulation space to node space, wherein said mapping comprises:
   identifying a cutoff area by cutting off pair interaction beyond a defined radius;
   ensuring that there exists at least one processor node for every pair of particles within the cutoff area that can calculate the pairwise interaction by identifying a minimal set of communicating nodes for a particular particle as those processor nodes which contain any of a volume of space centered about the particle;
   dividing the three-dimensional simulation space into a same number of voxels as processor nodes;
   determining a weight corresponding to a computational cost for a given pair interaction of particles in the simulation space at a midpoint between the interacting particles within the defined radius;
   assigning the determined weight to the midpoint in the simulation space between two interacting particles;
   performing a spatial partitioning of a volume of the simulation space such that all partitions have substantially the same weight; and
   assigning a computation of the pair interaction to the processing node owning the voxel that contains the midpoint of a line connecting the interacting pair of particles; and
   broadcast the position of each particle to points in the simulation space within a distance of one-half of the cut-off radius.

10. The computer program product of claim 9 wherein the code further causes the computer to perform the spatial portioning using a k-d tree on the simulation space.

11. The computer program product of claim 9 wherein the code further causes the computer to assign a weight to centers of the groups of fragments.

12. The computer program product of claim 9 wherein each of the fragments comprises a single particle.

13. The computer program product of claim 9 wherein the code further causes the computer to broadcast the position of a particle to a group of nodes containing a portion of a sphere having a radius Rb that is greater than Rc/2, where Rc is the defined radius to ensure the existence of at least one node containing the positions of both particles in a fragment pair required to compute any interaction.

14. The computer program product of claim 9 wherein the code further causes the computer to, when more than one node contains positions required to compute a particle interaction, assign the computation to any of those nodes, providing an opportunity for eliminating imbalances caused by short term local fluctuations in interaction workload.

* * * * *